US00RE38860E

(19) United States
(12) Reissued Patent
Shimada

(10) Patent Number: US RE38,860 E
(45) Date of Reissued Patent: Nov. 1, 2005

(54) SCANNING OPTICAL MICROSCOPE

(75) Inventor: Yoshihiro Shimada, Sagamihara (JP)

(73) Assignee: Olympus Optical Co., Ltd., Tokyo (JP)

(21) Appl. No.: 10/613,664

(22) Filed: Jul. 2, 2003

Related U.S. Patent Documents

Reissue of:
(64) Patent No.: 6,255,646
Issued: Jul. 3, 2001
Appl. No.: 09/401,203
Filed: Sep. 22, 1999

(30) Foreign Application Priority Data

Sep. 24, 1998 (JP) ..... 10-269561

(51) Int. Cl.[7] ..... G01J 3/28
(52) U.S. Cl. ..... 250/234; 356/300
(58) Field of Search ..... 250/234–236, 250/201.3, 458.1; 356/300, 310, 319, 320, 326

(56) References Cited

U.S. PATENT DOCUMENTS 5,127,730 A * 7/1992 Brelje et al. ..... 356/318
5,283,433 A * 2/1994 Tsien ..... 250/234
5,885,840 A * 3/1999 Kamentsky et al. ..... 436/63
6,128,077 A * 10/2000 Jovin et al. ..... 356/310
6,134,002 A * 10/2000 Stimson et al. ..... 356/326

FOREIGN PATENT DOCUMENTS

JP 53-135660 11/1978
JP 4-350816 A 12/1992
JP 5-509417 A 12/1993
JP 8-043739 A * 2/1996
JP 9-502269 * 3/1997

* cited by examiner

*Primary Examiner*—Stephone B. Allen
(74) *Attorney, Agent, or Firm*—Frishauf, Holtz, Goodman & Chick, PC

(57) ABSTRACT

A scanning optical microscope comprising a laser source, a scan optical system for scanning a sample with a laser beam from the laser source, a spectral resolving optical system for resolving spectra of fluorescent rays from the sample, a wavelength splitting optical system for splitting the fluorescent rays that have passed the spectral resolving optical system into rays of a plurality of different wavelengths and guiding the split rays to optical paths of the plurality of different wavelengths, a plurality of image forming optical systems, respectively provided in the optical paths of the plurality of different wavelengths, for forming images of the fluorescent rays from the sample, a plurality of confocal apertures respectively provided in the optical paths at focal points of the image forming optical systems, and a plurality of photosensors, respectively provided in the optical paths, for sensing the fluorescent rays from the sample that have passed the respective confocal apertures.

10 Claims, 6 Drawing Sheets

SCANNING OPTICAL MICROSCOPE

Matter enclosed in heavy brackets [ ] appears in the original patent but forms no part of this reissue specification; matter printed in italics indicates the additions made by reissue.

CROSS REFERENCE TO RELATED APPLICATION

This application claims the priority of Japanese Patent Application No. 98/269561 filed on Sep. 24, 1998, which is incorporated herein by reference.

BACKGROUND OF THE INVENTION

The present invention relates to a scanning optical microscope which disperses the fluorescence from a sample into a plurality of wavelength ranges and detects the fluorescence of each wavelength range.

The recent fluorescent observation often uses multiple dyes as well as a single dye. Since fluorescent dyeing is performed to permit cells or a specific target in an organ to be observed, each dyed portion should be detected as a clear color difference or a clear difference in fluorescent wavelength in the multiple dye observation. In this case, it is necessary to effectively remove the partial overlapping of the fluorescent wavelengths (crossover portion) in the detection. The fluorescent observation also demands a high contrast and high optical resolution. Confocal scanning laser microscopes satisfy those requirements and are becoming popular in researches in the field of biology.

Confocal scanning laser microscopes to which this invention relates and which can ensure fluorescent observation are disclosed in Jpn. Pat. Appln. Kokai Publication Nos. Hei 8-43739 and Hei 9-502269. Those microscopes use spectral resolving means like a prism or diffraction grating as fluorescence separation means for multiple dyes, and a slit for restricting the fluorescent wavelength range. This can ensure highly efficient detection of fluorescent rays from a multi-dyed sample without crossover while achieving the high contrast and high resolution of a confocal microscope.

The fluorescence from a sample is generally so weak that a photomultiplier is needed as a photosensor. Because the discoloration of a fluorescent sample becomes stronger as the excited light (laser beam) irradiated on the sample gets stronger. Therefore, an observer normally checks the balance of the discoloration of the sample and the acquired image noise and tries to make the amount of excited light as small as possible within the allowable range. For this kind of microscope, therefore, it is very important to suppress the fluorescent loss as much as possible.

We will now discuss a sample marked with two fluorescent dyes (DAPI, CY5) as one example. DAPI has an absorption wavelength in the UV range (340 to 365 nm) and an emitted fluorescent wavelength whose peak appears at approximately 450 nm. CY5 has an absorption wavelength in the red range (630 to 650 nm) and a fluorescent wavelength whose peak appears at approximately 670 nm.

The size of the spot which is formed at the position where those fluorescent rays form an image (where a confocal aperture is provided) is given by the following equation in, for example, Jpn. Pat. Appln. Kokai Publication No. Hei 9-502269.

$$Ø=1.22\times\lambda/NA$$

where NA is the numerical aperture for emission of a lens and $\lambda$ is the wavelength. The comparison of the spot size of DAPI (fluorescent wavelength of 450 nm) with that of CY5 (fluorescent wavelength of 670 nm), both calculated from the above equation, show that the spot size of CY5 is about 1.5 time greater than that of DAPI.

According to the above-described prior art, therefore, the size of a confocal aperture is set in accordance with the spot size of DAPI in order to secure the confocal effect. This means that the setting of the confocal aperture is set optimized for DAPI, but is too narrow for CY5, resulting in loss of precious fluorescence. Setting the size of the confocal aperture for CY5, on the other hand, would result in an insufficient confocal effect for DAPI.

The bundle of rays that have passed the confocal aperture is resolved by the spectral resolving means (prism) and is split into wavelengths of the individual fluorescent rays using a variable slit. When a prism is used as the spectral resolving means, however, if the size of the bundle of incident rays is large, crossover of the individual wavelengths after spectral resolving occurs, the bundle of rays would not be split into the individual photosensing paths at a sufficient precision.

BRIEF SUMMARY OF THE INVENTION

Accordingly, it is a primary object of the present invention to provide a scanning optical microscope capable of leading rays of individual fluorescent wavelengths of a multi-dyed sample to the respective photosensors without reducing the confocal effect and losing the fluorescence.

It is another object of the present invention to provide a scanning optical microscope capable of leading a bundle of rays of individual fluorescent wavelengths of a multi-dyed sample to the respective photosensing paths at a high precision.

To achieve the above object, according to the main aspect of this invention, there is provided a scanning optical microscope which comprises a laser source; a scan optical system for scanning a sample with a laser beam from the laser source; a spectral resolving optical system for resolving spectra of fluorescent rays from the sample; a wavelength splitting optical system for splitting the fluorescent rays that have passed the spectral resolving optical system into rays of a plurality of different wavelengths and guiding the split rays to optical paths of the plurality of different wavelengths; a plurality of image forming optical systems, respectively provided in the optical paths of the plurality of different wavelengths, for forming images of the fluorescent rays from the sample; a plurality of confocal apertures respectively provided in the optical paths at focal points of the image forming optical systems; and a plurality of photosensors, respectively provided in the optical paths, for sensing the fluorescent rays from the sample that have passed the respective confocal apertures.

With this structure, the individual fluorescent rays from a multi-dyed sample are separated and guided to optical paths of the wavelength ranges of the respective fluorescent rays. As an image forming optical system for forming an image of the associated fluorescent ray from the sample and a confocal aperture are provided in the associated optical path, each confocal aperture can be set to the optimal aperture size for the associated wavelength range. This can provide a perfect confocal effect without any fluorescence loss.

According to one mode of the scanning optical microscope, the spectral resolving optical system includes a first optical element for resolving the spectra of the fluorescent rays from the sample; and a second optical element for transforming a bundle of rays resulting from spectral resolving by the first optical element back to a bundle of parallel rays.

As this structure allows a bundle of rays undergone spectral resolving and wavelength splitting to be emitted in parallel to the respective photosensing paths, those parallel rays all focus on the confocal points. Therefore, a scanning optical microscope can be constructed by simply arranging the confocal apertures to the respective confocal points. Since an independent confocal optical system can be provided in each path by merely arranging a single confocal aperture and a single photosensor in the optical path following the stage of separating the bundle of rays, the microscope can be constructed easily and at a low cost.

According to another mode of the scanning optical microscope, a reducing optical system for reducing a bundle of rays incident to the spectral resolving optical system is provided closer to a sample side than the spectral resolving optical system.

This structure improves the spectral resolving precision. It is preferable that the reduction ratio of this reducing optical system is at least 1/2. When the interval between the first and second optical elements is narrow, the reduction ratio is set smaller.

According to a further mode of the scanning optical microscope, the numbers of the image forming optical systems, the confocal apertures and the photosensors are equal to the number of fluorescent rays to be sensed; and the wavelength splitting optical system has wavelength splitting optical elements smaller in number by one than the number of the photosensors.

This setting can provide a microscope having a desired number of channels.

According to a modification of the third mode, the scanning optical microscope further comprises an optical-element positioning drive mechanism for positioning the wavelength splitting optical elements in a direction perpendicular to an incident optical axis.

This structure can facilitate microadjustment of the optical elements to ensure high-precision ray sensing.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Preferred embodiments of this invention will be described below with reference to the accompanying drawings.

First Embodiment

A first embodiment of this invention will now be discussed referring to FIGS. 1 through 5.

Figure 1:
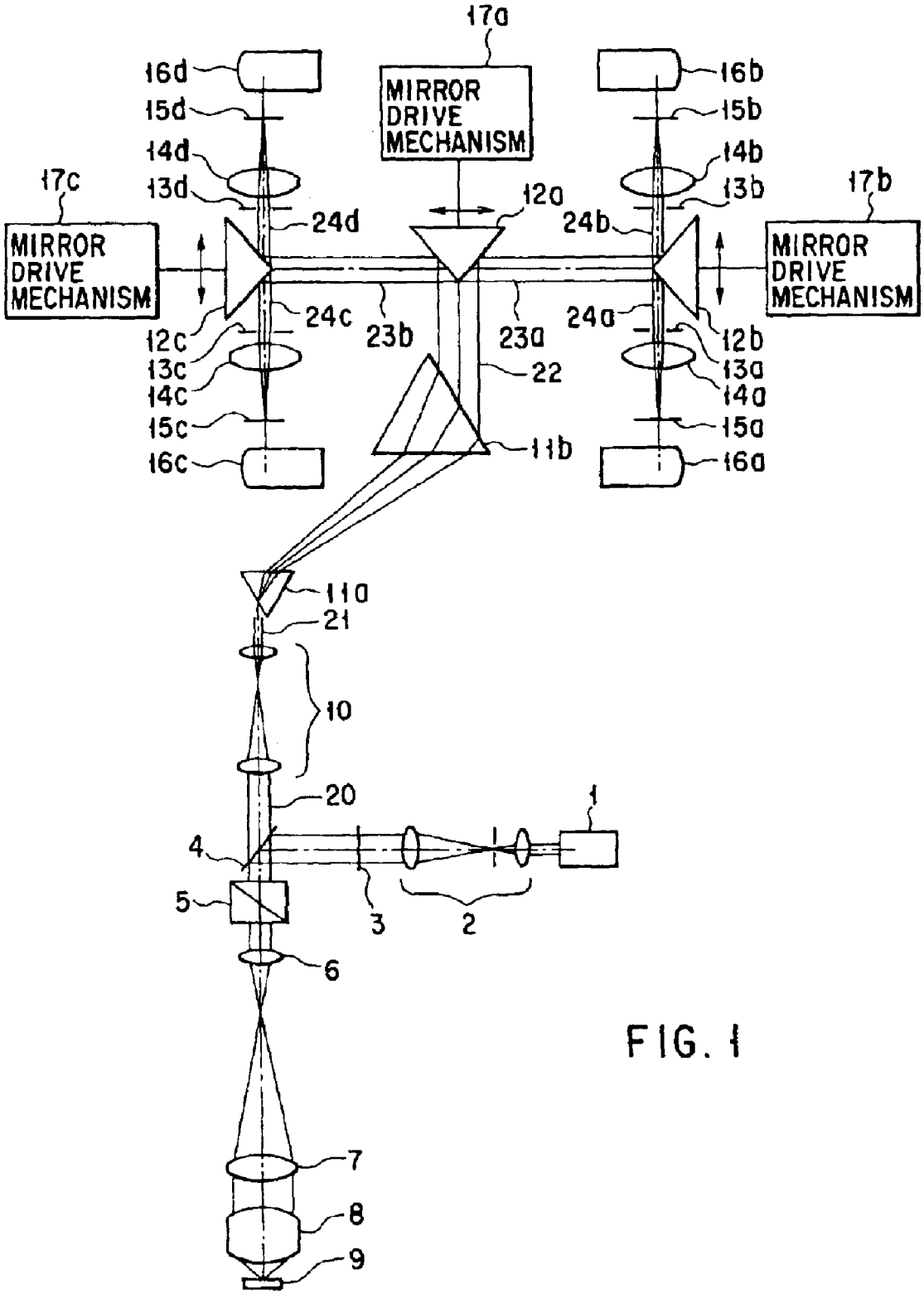
FIG. 1 is a structural diagram of a scanning optical microscope according to a first embodiment of this invention.

FIG. 1 shows the general structure of a scanning optical microscope according to this first embodiment.

FIG. 1 shows a typical laser source 1 which is comprised of an argon-krypton gas laser. The laser beam that has been emitted from this laser source 1 sequentially passes a beam expander 2, a wavelength-selection filter 3, a beam splitter 4, an X-Y scan optical system 5, a pupil projection lens 6, an image-forming lens 7 and an objective lens 8 and reaches a sample 9.

The laser source 1 emits argon rays of mainly 351 nm and 488 nm and krypton rays of 568 nm and 647 nm. The beam expander 2 is set in such a way that the size of the laser beam nearly satisfies the pupil size of the objective lens 8. The beam splitter 4 reflects about 20% of the arrived light and passes about 80% of that light.

The wavelength-selection filter 3 selectively passes rays of a wavelength of 351 nm, 488 nm, 568 nm or 647 nm. For example, the sample 9 is dyed with four dyes, DAPI, FITC, Texas Red and CY5; DAPI is excited by the argon rays of 351 nm, FITC by the argon rays of 488 nm, Texas Red by the krypton rays of 568 nm and CY5 by the krypton rays of 647 nm.

When excited, DAPI emits fluorescent rays which have a peak at approximately 450 nm. Likewise, FITC emits fluorescent rays having a peak at approximately 530 nm, Texas Red emits fluorescent rays having a peak at approximately 610 nm, and CY5 emits fluorescent rays having a peak at approximately 670 nm. Those fluorescent rays pass through the beam splitter 4 after passing the objective lens 8, the image-forming lens 7, the pupil projection lens 6 and the X-Y scan optical system 5.

A bundle of rays 20 that have passed the beam splitter 4 travels through a reducing optical system 10 which reduces the bundle of rays, thus forming a bundle of parallel rays 21. This bundle of parallel rays 21 passes a prism 11a for spectral resolving, and a bundle of rays with the resolved spectra is formed into a bundle of parallel rays 22 by a prism 11b which is optically identical to the prism 11a. The bundle of parallel rays 22 then reaches a first prism mirror 12a. The first prism mirror 12a is so designed as to be movable in a direction perpendicular to the incident axis by a first mirror drive mechanism 17a, and is set in such a manner that the bundle or rays is separated into right and left optical paths with about 570 nm as the boundary. Consequently, the fluorescent rays of DAPI and FITC are separated as a bundle of rays 23a, while the fluorescent rays of Texas Red and CY5 are separated as a bundle of rays 23b.

The bundle of parallel rays 23a enters a second prism mirror 12b. This second prism mirror 12b is likewise so designed as to be movable in a direction perpendicular to the incident axis by a second mirror drive mechanism 17b, and is set in such a manner that the bundle of rays is separated into right and left optical paths with about 490 nm as the boundary. As a result, the fluorescent rays of DAPI are separated as a bundle of rays 24a, and the fluorescent rays of FITC are separated as a bundle of rays 24b.

The other bundle of parallel rays 23b likewise enters a third prism mirror 12c. This third prism mirror 12c is also so designed as to be movable in a direction perpendicular to the incident axis by a third mirror drive mechanism 17c, and is set in such a manner that the bundle of rays is separated into right and left optical paths with about 650 nm as the boundary. Consequently, the fluorescent rays of Texas Red are separated as a bundle of rays 24c, and the fluorescent rays of CY5 are separated as a bundle of rays 24d.

The individual bundles of rays 24a, 24b, 24c and 24d pass through slits 13a, 13b, 13c and 13d, which have variable widths and are each movable in a direction perpendicular to the optical axis, so that the return rays of the excited rays from the sample and partial overlapping portions of the fluorescent wavelengths (crossover portions of the fluorescent rays) are restricted by those slits 13a–13d. The individual bundles of fluorescent rays 24a, 24b, 24c and 24d that have passed the slits 13a, 13b, 13c and 13d reach confocal lenses 14a, 14b, 14c and 14d respectively. As the bundles of fluorescent rays 24a, 24b, 24c and 24d are emitted as bundles of parallel rays, they focus on confocal apertures 15a, 15b, 15c and 15d located at their focal points, and pass through the confocal apertures 15a–15d to be sensed by photomultipliers 16a, 16b, 16c and 16d.

The aperture sizes of the confocal apertures 15a–15d are set to the ones that are calculated by the following equation.

$$Ø=1.22\times\lambda/NA$$

where NA is the numerical aperture for emission of each of the confocal lenses 14a, 14b, 14c and 14d and $\lambda$ is the fluorescent wavelength.

With this structure where the confocal lenses 14a, 14b, 14c and 14d and the confocal apertures 15a, 15b, 15c and 15d are respectively arranged in the individual fluorescent optical paths for DAPI, FITC, Texas Red and CY5, for example, the aperture sizes Ø of the confocal apertures 15a, 15b, 15c and 15d can be set optimally for the respective fluorescent rays. It is thus possible to provide the best confocal effect without losing the fluorescence.

As the above structure has the reducing optical system 10 provided immediately before the first prism 11a, ray sensing can be implemented with a higher precision.

If the beam size of the bundle of rays 21 incident to the first prism 11a is large, the spectra resolved by the first prism 11a may overlap, disabling the optimal dispersion for each fluorescent frequency by the prism mirror 12a. This embodiment does not however suffer such a problem because the reducing optical system 10 which reduces the beam size of the incident bundle of rays to at least ½ is provided immediately before the first prism 11a.

Figure 3:
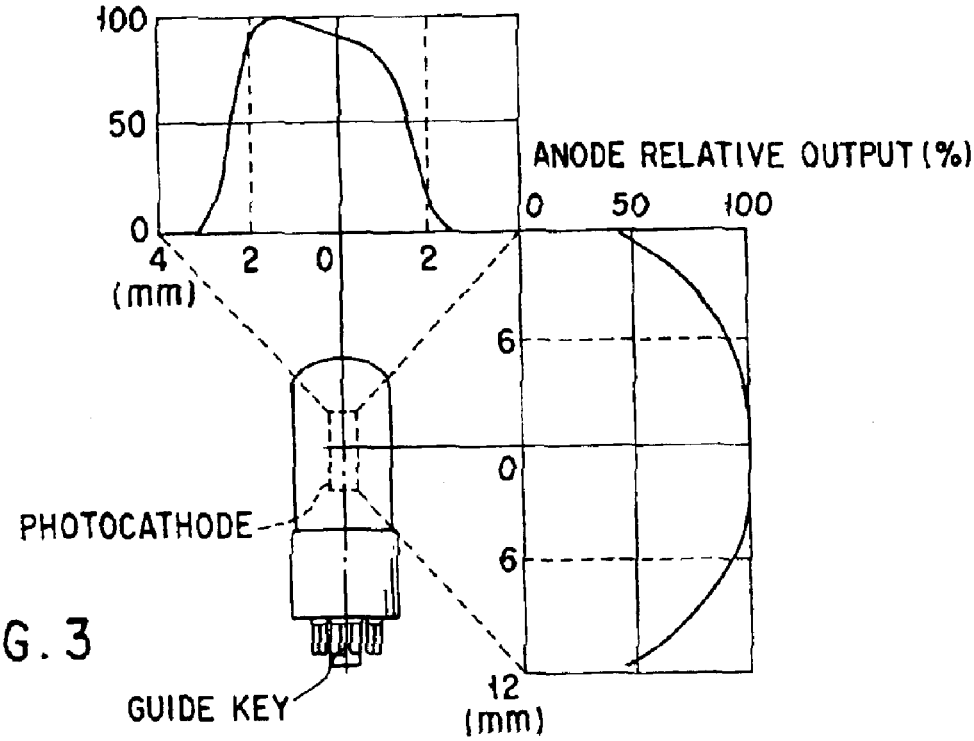
FIG. 3 is a diagram showing sensitivity distribution data of a side-on type photomultiplier according to the first embodiment.

The photomultipliers 16a, 16b, 16c and 16d are of a side-on type and have their axial centers coming approximately within planes to be spectral-resolved by the prism 11a. The side-on type photomultipliers, which are generally highly sensitive, are cheaper than head-on type photomultipliers, and are often used in scanning confocal laser microscopes. However, the side-on type photomultipliers are inferior to the head-on type photomultipliers in a large difference between the axial and vertical sensitivities, though there is not much difference in the axial sensitivity distribution. As a reference, the sensitivity distribution data of the side-on type photomultiplier is shown in FIG. 3.

Since the axial centers of the side-on type photomultipliers come approximately within the planes to be spectral-resolved by the prism 11a in this embodiment, the sensitivity distribution of the side-on type photomultipliers is hardly significant.

Although the foregoing description has discussed a way of guiding the individual fluorescent rays to the respective sensing paths in a case where the sample 9 is dyed with flour dyes, this invention can also cope with a case where the sample 9 is dyed with a single dye without any difficulty. When the sample 9 is dyed with a single dye of FITC, crossover with the other fluorescent rays need not be considered, so all the fluorescent rays to be acquired have only to be guided to a single photosensor.

Figure 2:
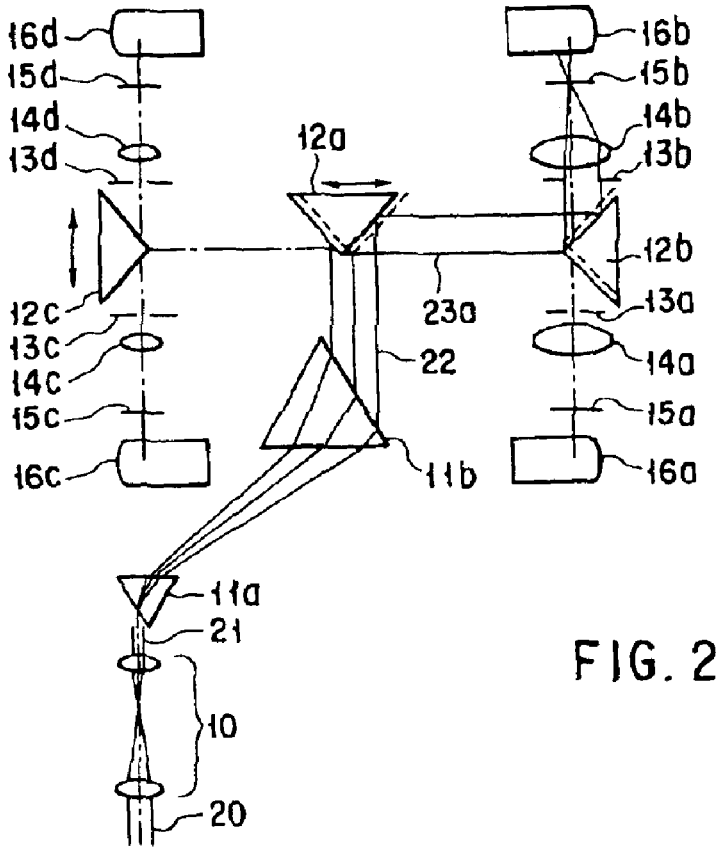
FIG. 2 is a structural diagram of the scanning optical microscope according to the first embodiment.

In this case, positions of the prism mirrors 12a and 12b should be adjusted as shown in FIG. 2 so that FITC can be acquired completely. In FIG. 2, like or same reference numerals are given to those components which are the same as the corresponding components in FIG. 1. As the structure below the reducing optical system 10 is the same as the one shown in FIG. 1, it is not illustrated in FIG. 2.

If rays of 600 nm or lower are acquired completely, for example, fluorescent rays of FITC can be gotten completely, so that the positions of the prism mirrors 12a and 12b are so set as to be able to get rays of 600 nm or lower. The slit 13b has only to be set to cut the excited light of 488 nm and get light of 600 nm or lower. This invention can also easily be adapted to cases of a double-dyed sample and a triple-dyed sample.

Although a pair of prisms 11a and 11b which are optical identical are used as the spectral resolving optical system in the first embodiment, a pair of diffraction gratings or a pair of holograms which are optical identical to each other may be used as well. As the bundle of rays undergone spectral resolving should be emitted as a bundle of parallel rays, different optical elements like a prism and a diffraction grating may be combined.

Figure 4:
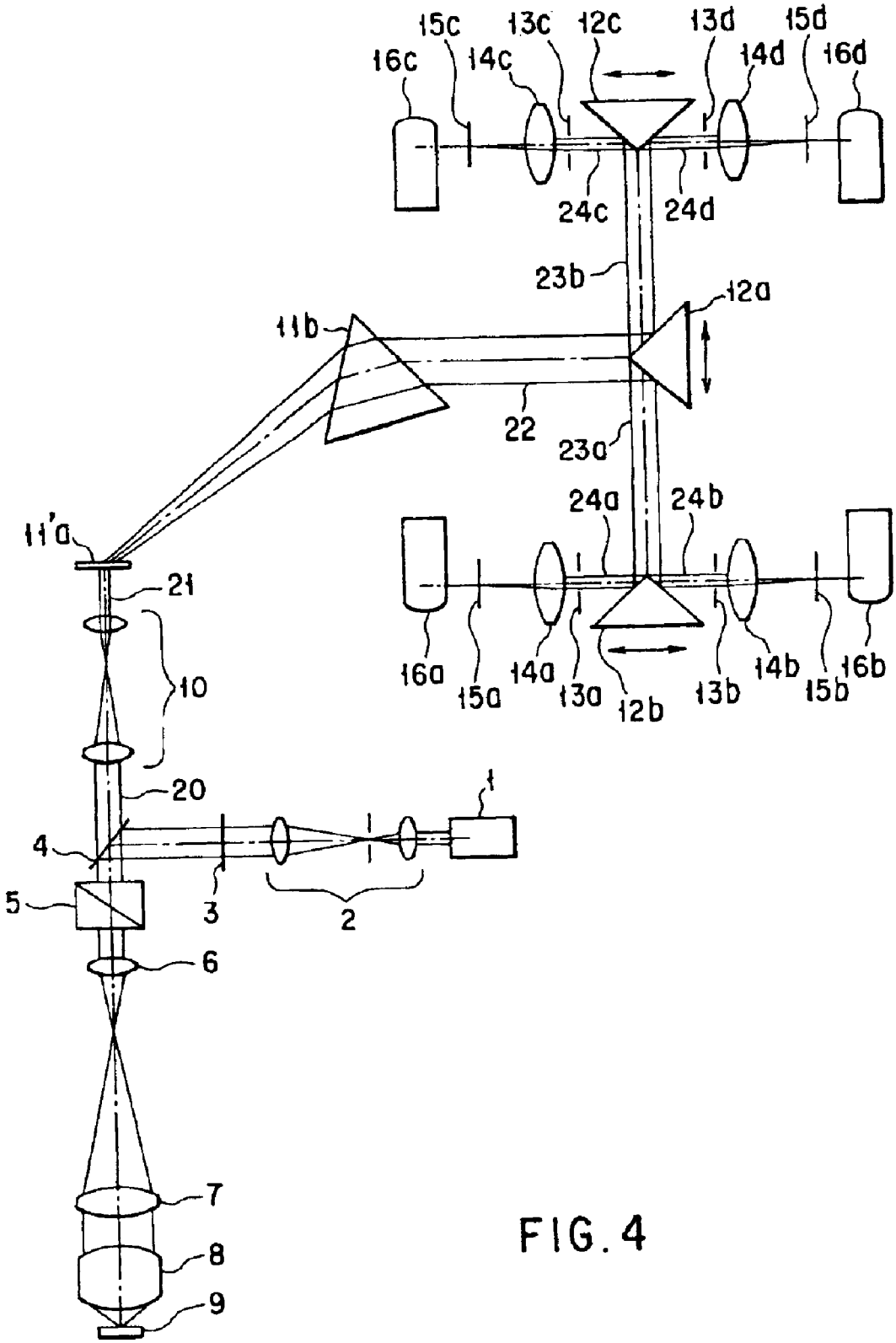
FIG. 4 is a structural diagram showing of a modification of the first embodiment.

FIG. 4 shows an optical system which is a combination of a prism and a diffraction grating. In this case, since the diffraction directions of the prism and diffraction grating are opposite to each other, the axis of the outgoing bundle of rays forms, for example 90 degrees to the axis of the incident bundle of rays if one wants to acquire a bundle of parallel rays for each fluorescence.

Figure 5:
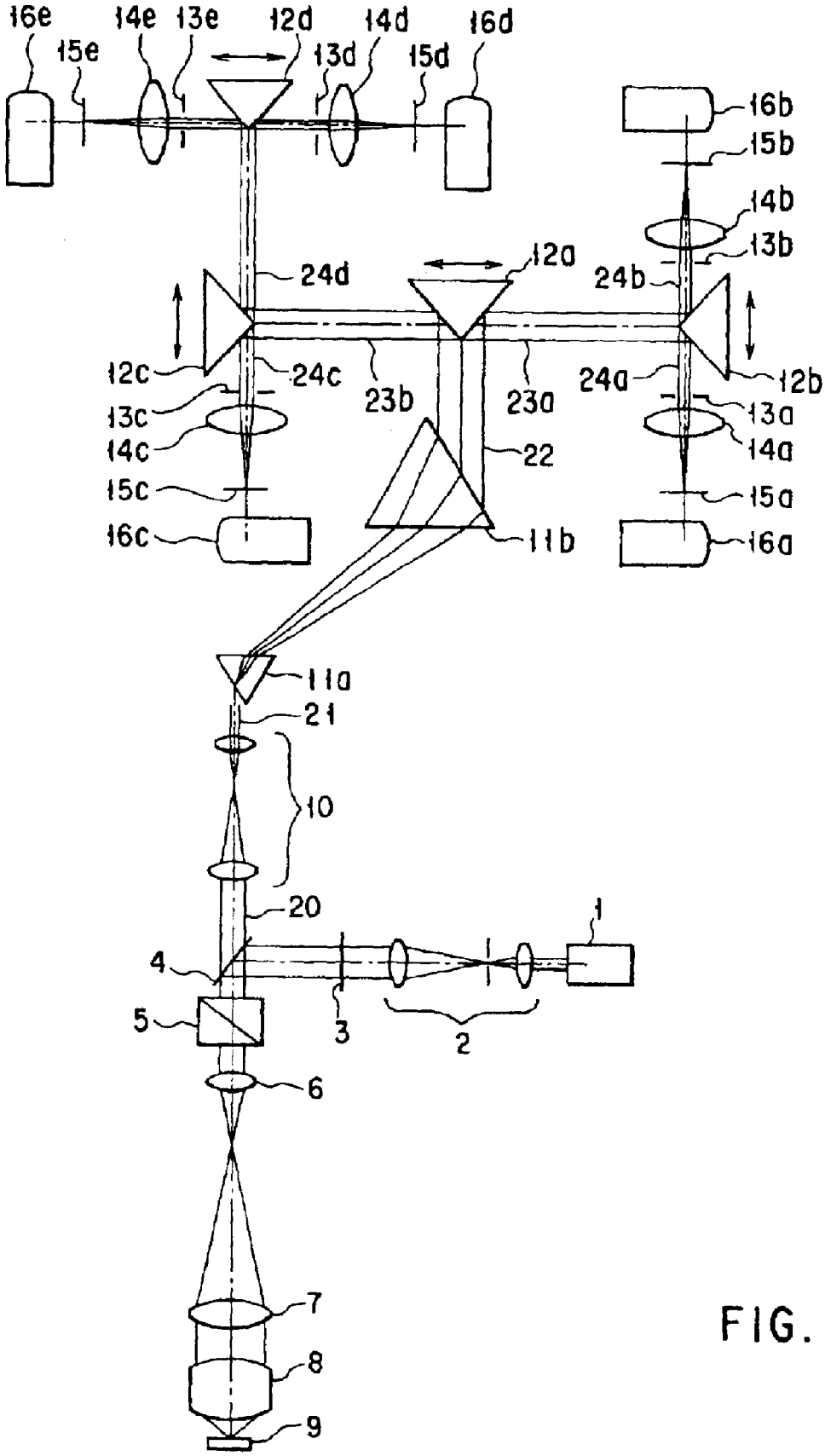
FIG. 5 is a structural diagram showing of another modification of the first embodiment.

Because the fluorescent rays can be split into a plurality of wavelengths by prism mirrors according to the above-described first embodiment, the number of fluorescence sensing paths can be set as desired. Although this example has a four-channel structure, it can easily be modified into a two-channel structure, 3-channel structure, 5-channel structure and so forth. FIG. 5 shows a case of the 5-channel structure. In this example, the bundle of rays separated by the third prism mirror 12c is further separated by a fourth prism mirror 12d into two bundles of rays which respectively pass slits 13d and 13e, confocal lenses 14d and 14e and confocal apertures 15d and 15e to be respectively detected by photomultipliers 16d and 16e. This structure can provide five fluorescence sensing paths.

Since the axial centers of the side-on photomultipliers come approximately within the planes to be spectral-resolved by the prism 11a, the sensitivity distribution is hardly significant. The use of such cheap side-on type photomultipliers can realize an inexpensive scanning optical microscope.

Second Embodiment

Figure 6:
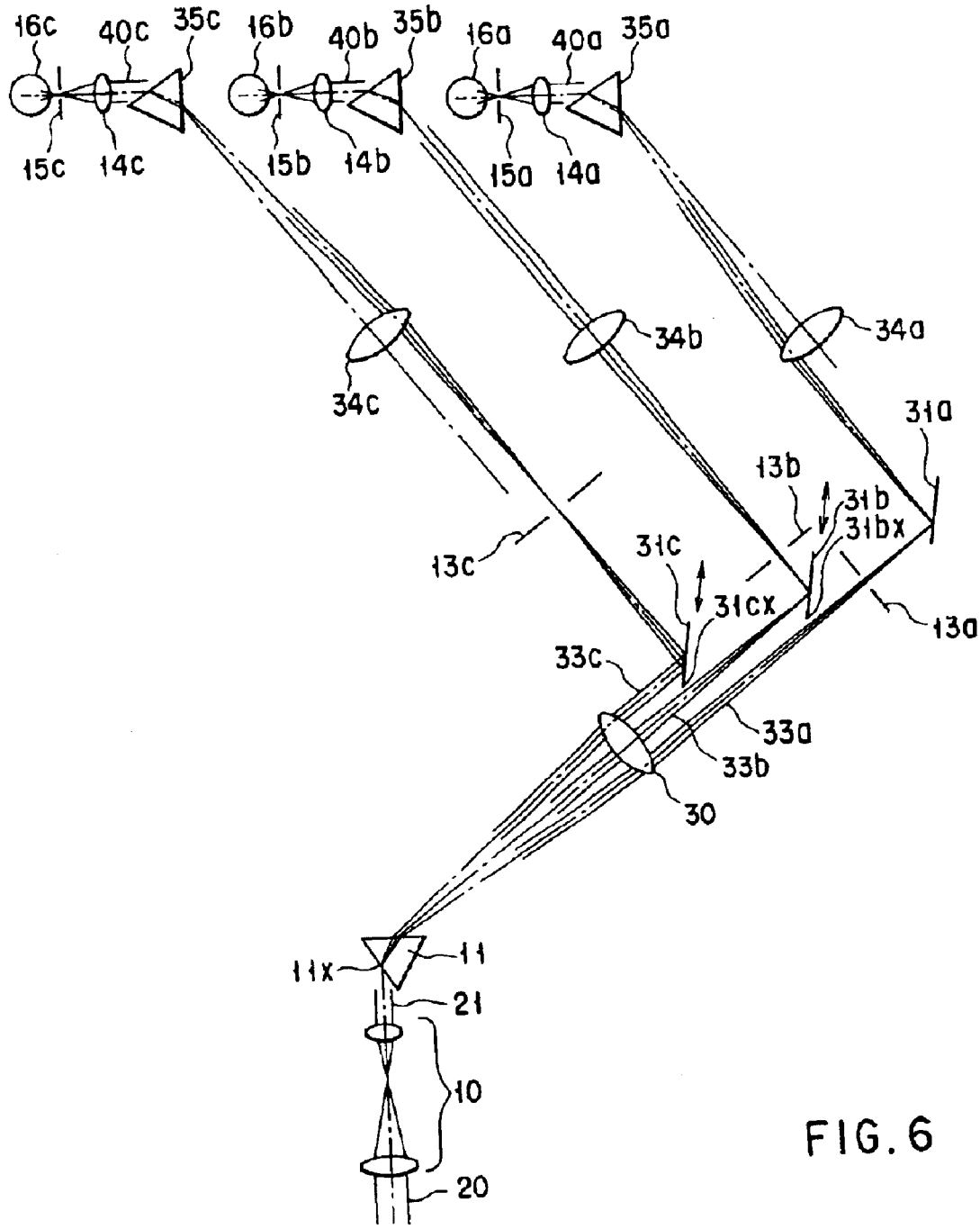
FIG. 6 is a diagram illustrating the structure of a scanning optical microscope according to a second embodiment of this invention.
Figure 7:
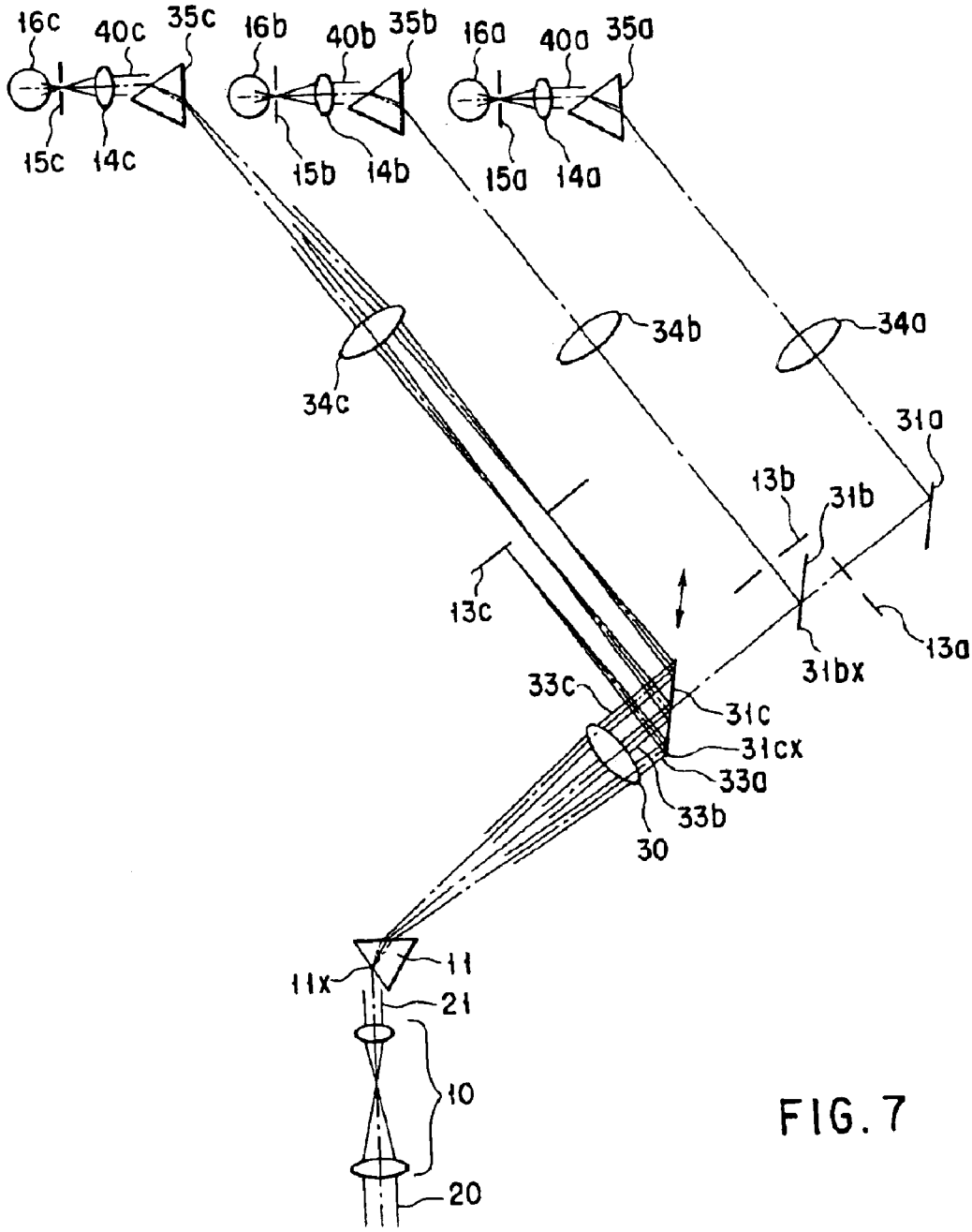
FIG. 7 is a diagram illustrating the structure of the scanning optical microscope according to the second embodiment of this invention.

FIGS. 6 and 7 show the structure of a scanning optical microscope according to a second embodiment of this invention. In FIGS. 6 and 7, like or same reference numerals are given to corresponding or identical components. As the structure below the reducing optical system 10 in FIGS. 6 and 7 is the same as the one in FIG. 1, its illustration is omitted.

A laser source 1 shown in FIG. 6 is a light source for an argon-krypton gas. The laser beam that has been emitted from this laser source 1 sequentially passes a beam expander 2, a wavelength-selection filter 3, a beam splitter 4, an X-Y scan optical system 5, a pupil projection lens 6, an image-forming lens 7 and an objective lens 8 and reaches a sample 9.

The laser source 1 emits argon rays of mainly 488 nm and krypton rays of 568 nm and 647 nm. The beam expander 2 is set in such a way that the size of the laser beam nearly satisfies the pupil size of the objective lens 8. The beam splitter 4 reflects about 20% of the arrived light and passes about 80% of that light.

The wavelength-selection filter 3 selectively passes rays of a wavelength of 488 nm, 568 nm or 647 nm. For example, the sample 9 is triple-dyed with FITC, Texas Red and CY5; FITC is excited by the argon rays of 488 nm. Texas Red by the krypton rays of 568 nm and CY5 by the krypton rays of 647 nm.

When excited, FITC emits fluorescent rays which have a peak at approximately 530 nm. Likewise, Texas Red emits fluorescent rays having a peak at approximately 610 nm, and CY5 emits fluorescent rays having a peak at approximately 670 nm. Those fluorescent rays pass through the beam splitter 4 after passing the objective lens 8, the image-forming lens 7, the pupil projection lens 6 and the X-Y scan optical system 5.

As shown in FIG. 6, a bundle of rays 20 that have passed the beam splitter 4 travels through a reducing optical system 10 which reduces the bundle of rays, thus forming a bundle of parallel rays 21. This bundle of parallel rays 21 passes a prism 11 for spectral resolving, and the resultant bundle of rays enters a lens 30. The lens 30 is arranged in such a way that its focal point coincides with an incident point 11x of the bundle of rays to the prism 11. Therefore, the individual spectral-resolved bundles of rays from the lens 30 are emitted as bundles of parallel rays within the spectral-resolved planes. The spectral-resolved bundles of rays are separated by mirrors 31a, 31b and 31c to go to the respective fluorescence sensing paths. The mirrors 31b and 31c are movable in a direction of 45° with respect to the incident light axis.

Specifically, an end face 31cx of the mirror 31c is set to a position where excited rays of approximately 647 nm bit, and an end face 31bx of the mirror 31b is set to a position where excited rays of approximately 568 nm bit. This structure allows the fluorescent rays of FITC to be separated as a bundle of rays 33a, the fluorescent rays of Texas Red to be separated as a bundle of rays 33b, and the fluorescent rays to CY5 to be separated as a bundle of rays 33c. Although the positions of the mirrors 31a, 31b and 31c are slightly shifted from the focal point of the lens 30, ray separation to the individual fluorescence sensing paths can be executed with a sufficiently high precision because the size of the bundle of rays is reduced by the reducing optical system 10.

The individual bundles of rays 33a, 33b and 33c pass through slits 13a, 13b and 13c, which have variable widths and are each movable in a direction perpendicular to the optical axis, so that the return rays of the excited rays from the sample and partial overlapping portions of the fluorescent wavelengths (crossover portions of the fluorescent rays) are removed by those slits 13a–13c. The slits 13a, 13b and 13c are located at the focal point of the lens 30. As the individual bundles of rays after spectral resolving form spots at the positions of the respective slits, the slits can restrict the wavelengths with a very high precision. The positions of the slits 13a to 13c and the mirrors 31a to 31c may be set in such a way that the focal point of the lens 30 comes to an intermediate position thereof.

The individual bundles of rays that have passes the slits pass lenses 34a, 34b, 34c and prism 35a, 35b and 35c. The lenses 34a, 34b, 34c are identical to the lens 30 and the prisms 35a, 35b and 35c are identical to the prism 11. The spectral-resolved bundles of rays are combined in the individual optical paths to respectively become bundles of rays 40a, 40b and 40c, which enter confocal lenses 14a, 14b and 14c. The bundles of rays 40a, 40b and 40c then pass confocal apertures 15a, 15b and 15c, arranged at their focal points, and are sensed by photomultipliers 16a, 16b and 16c that are so arranged that their axes become perpendicular to the sheet.

As the spectra of the bundles of rays 40a, 40b and 40c are completely combined, unlike in the first embodiment, the bundles of rays 40a, 40b and 40c do not spread toward the spectral resolving direction after passing the confocal apertures 15a, 15b and 15c. Therefore, no problem would arise even if the photomultipliers 16a, 16b and 16c are arranged in such a way that their axes become perpendicular to the sheet.

The aperture sizes of the confocal apertures are set to the ones that are calculated by the following equation.

$$Ø=1.22\times\lambda/NA$$

where NA is the numerical aperture for emission of each of the confocal lenses 14a, 14b, 14c and 14d and λ is the fluorescent wavelength.

Like the first embodiment, therefore, this embodiment can provide the best confocal effect without losing the fluorescent rays of FITC, Texas Red and CY5. Although the illustrated example has a 3-channel structure, the number of channels is not limited to three but can be set arbitrarily according to the purpose.

Although the foregoing description has discussed a way of guiding the individual fluorescent rays to the respective sensing paths in a case where the sample 9 is dyed with three dyes, this invention can also cope with a case where the sample 9 is dyed with a single dye without any difficulty. When the sample 9 is dyed with a single dye of FITC, crossover with the other fluorescent rays need not be considered, so all the fluorescent rays to be acquired have only to be guided to a single photosensor.

In this case, the position of the mirror 31c should be adjusted as shown in FIG. 7 so that FITC can be acquired completely. If rays of 600 nm or lower are acquired completely, for example, fluorescent rays of FITC can be obtained completely, so that the position of the mirror 31c is so set as to be able to get rays of 600 nm or lower. The slit 13c has only to be set to cut the excited light of 488 nm and get light of 600 nm or lower. This invention can also easily be adapted to cases of a double-dyed sample and a triple-dyed sample.

Although a prism is used as the spectral resolving means in the second embodiment, a diffraction grating or a hologram may be used as well.

Since the spectral-resolved bundle of rays is formed as a spot by the image-forming lens 30 in the second embodiment, it is possible to restrict the wavelengths of fluorescent rays with very high precision. As the focal point of the lens 30 is set to match with the incident position 11x of the bundle of rays 21 to the prism 11, the spectral-resolved bundle of rays emitted from the lens 30 become parallel in the spectral-resolved plane. This can allow the use of the lenses 34a, 34b and 34c each identical to the lens 30 and the prisms 35a, 35b and 35c each identical to the prism 11, so that the microscope can be constructed easily and at a low cost.

It should be apparent to those skilled in the art that the present invention is not limited to the above-described embodiments, but may be embodied in many other specific forms without departing from the spirit or scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A scanning optical microscope comprising:

a laser source;

a scan optical system for scanning a sample with a laser beam from said laser source;

a spectral resolving optical system for resolving spectra of fluorescent rays from said sample;

a wavelength splitting optical system for splitting said fluorescent rays that have passed said spectral resolving optical system into rays of a plurality of different wavelengths and guiding said split rays to optical paths of said plurality of different wavelengths;

a plurality of image forming optical systems, respectively provided in said optical paths of said plurality of different wavelengths, for forming images of said fluorescent rays from said sample;

a plurality of confocal apertures respectively provided in said optical paths at focal points of said image forming optical systems; and a plurality of photosensors, respectively provided in said optical paths, for sensing said fluorescent rays from said sample that have passed the respective confocal apertures.

2. The scanning optical microscope according to claim 1, wherein said spectral resolving optical system includes:

a first optical element for resolving said spectra of said fluorescent rays from said sample; and a second optical element for transforming a bundle of rays resulting from spectral resolving by said first optical element back to a bundle of parallel rays.

3. The scanning optical microscope according to claim 1, further comprising a reducing optical system, provided closer to a sample side than said spectral resolving optical system, for reducing a bundle of rays incident to said spectral resolving optical system.

4. The scanning optical microscope according to claim 1, wherein the numbers of said image forming optical systems, said confocal apertures and said photosensors are equal to the number of fluorescent rays to be sensed; and said wavelength splitting optical system has wavelength splitting optical elements smaller in number by one than said number of said photosensors.

5. The scanning optical microscope according to claim 4, further comprising an optical-element positioning drive mechanism for positioning said wavelength splitting optical elements.

6. The scanning optical microscope according to claim 5, wherein said optical-element positioning drive mechanism positions said wavelength splitting optical elements in a direction perpendicular to an incident optical axis.

*7. A scanning optical microscope which scans a sample with a laser beam from a laser source, said scanning optical microscope comprising:*

*a spectral resolving unit which resolves fluorescent rays from the sample into successive spectral components;*

*a wavelength splitter which splits the successive spectral components resolved by the spectral resolving unit into rays of a plurality of different wavelengths; and*

*a plurality of side-on type photomultipliers, respectively provided in optical paths of the rays of different wavelengths split by the wavelength splitter, for sensing the rays,*

*wherein axial centers of the plurality of side-on type photomultipliers come approximately within planes to be spectrally-resolved by the spectral resolving unit.*

*8. A scanning optical microscope which scans a sample with a laser beam from a laser source, said scanning optical microscope comprising:*

*a spectral resolving unit which resolves spectra of fluorescent rays from the sample;*

*a wavelength splitter which splits the fluorescent rays resolved by the spectral resolving unit into rays of a plurality of different wavelengths;*

*a plurality of side-on type photomultipliers, respectively provided in optical paths of the rays of different wavelengths split by the wavelength splitter, for sensing the rays, wherein axial centers of the plurality of side-on type photomultipliers come approximately within planes to be spectrally-resolved by the spectral resolving unit;*

*a plurality of image forming optical systems, respectively provided at fronts of the plurality of side-on type photomultipliers in each of the optical paths of the rays of different wavelengths split by the wavelength splitter, for forming images of the rays; and*

*a plurality of confocal apertures respectively provided at focal points of said plurality of image forming optical systems.*

*9. The scanning optical microscope of claim 8, wherein said spectral resolving unit comprises an optical unit which emits a resolved bundle of rays in parallel.*

*10. A scanning optical microscope which scans a sample with a laser beam from a laser source, said scanning optical microscope comprising:*

*a spectral resolving unit which resolves spectra of fluorescent rays from the sample;*

*a wavelength splitter which splits the fluorescent rays resolved by the spectral resolving unit into rays of a plurality of different wavelengths;*

*a plurality of side-on type photomultipliers, respectively provided in optical paths of the rays of different wavelengths split by the wavelength splitter, for sensing the rays, wherein axial centers of the plurality of side-on type photomultipliers come approximately within planes to be spectrally-resolved by the spectral resolving unit;*

*a beam splitter for splitting the fluorescent rays from the sample and the laser beam; and*

*a reducing optical system, provided between the beam splitter and said spectral resolving unit, for reducing the flourescent rays.*

* * * * *